United States Patent [19]

Moser

[11] 4,144,224

[45] Mar. 13, 1979

[54] PHOSPHONATE STABILIZERS

[75] Inventor: Paul Moser, Riehen, Switzerland

[73] Assignee: Ciba-Geigy Corporation, Ardsley, N.Y.

[21] Appl. No.: 852,273

[22] Filed: Nov. 17, 1977

[30] Foreign Application Priority Data

Nov. 26, 1976 [CH] Switzerland ................ 14922/76

[51] Int. Cl.$^2$ .............. C07D 211/44; C07D 211/58; C08K 5/34; C08K 5/53
[52] U.S. Cl. ................ 260/45.75 N; 260/45.75 G; 260/45.75 M; 260/45.75 Q; 260/45.75 R; 260/45.75 W; 260/45.8 NE; 260/45.8N; 544/64; 544/129; 544/130; 542/424; 546/22; 546/2; 546/24
[58] Field of Search .......... 260/293.87, 45.8 NP (U.S. only), 260/45.75 N (U.S. only)

[56] References Cited

U.S. PATENT DOCUMENTS

| 3,684,765 | 8/1972 | Matsui et al. ............ 260/293.87 |
| 3,759,926 | 9/1973 | Chalmers et al. ......... 260/293.66 |
| 3,852,297 | 12/1974 | Moser et al. ............ 260/45.75 N |
| 3,937,711 | 2/1976 | Cook ..................... 260/293.87 |
| 3,959,326 | 5/1976 | Moser et al. ............ 260/45.75 N |
| 4,001,181 | 1/1977 | Ramey et al. ............ 260/45.75 N |

*Primary Examiner*—Donald E. Czaja
*Assistant Examiner*—R. A. White
*Attorney, Agent, or Firm*—Joseph F. DiPrima; Vincent J. Cavalieri

[57] ABSTRACT

New amino phosphonates, containing 2,2,6,6-tetrasubstituted-piperidino moieties and processes for their manufacture are disclosed. These compounds are employed to stabilize organic materials such as polyolefins, polyamides and polyurethanes against degradation from the action of oxygen, heat and light.

12 Claims, No Drawings

PHOSPHONATE STABILIZERS

The present invention relates to new aminophosphonates, processes for their manufacture and their use as stabilisers and to organic material stabilised, with the aid of these compounds, towards light-induced and thermal degradation.

α-Amino-phosphonates are known as light stabilisers for polymers from German Offenlegungsschrift No. 2,443,400. However, these stabilisers cannot always meet the high demands made in practice, especialy with regard to their light stabilising action.

The object of the invention was to provide, starting from this state of the art, new stabilisers for polymers which, whilst they have an outstanding light stabilising action, display on discoloration in the substrate, are stable to heat and are difficult to extract from the substrate.

Accordingly, the invention relates to aminophosphonates of the formula I

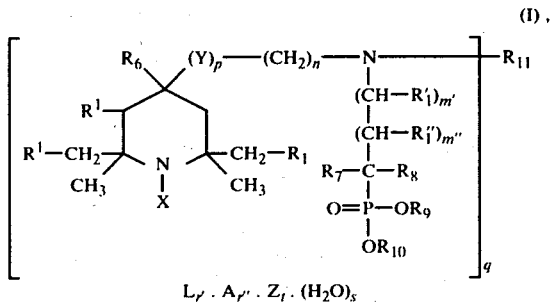

in which $R_1$, $R'_1$ and $R''_1$ in each case independently of one another are hydrogen or $C_1$-$C_4$-alkyl, X denotes hydrogen, oxyl, $C_1$-$C_{12}$-alkyl, $C_3$-$C_6$-alkenyl, $C_3$-$C_4$-alkinyl, $C_2$-$C_{21}$-alkoxyalkyl, $C_7$-$C_8$-aralkyl, 2,3-epoxypropyl, an aliphatic acyl group with 1-4 C atoms or one of the groups —$CH_2COOR_2$, —$CH_2$—$CH(R_3)$—$OR_4$, —$COOR_5$ or —$CONHR_5$, in which $R_2$ is $C_1$-$C_8$-alkyl, $C_3$-$C_6$-alkenyl, phenyl, $C_7$-$C_8$-aralkyl or cyclohexyl and $R_3$ is hydrogen, methyl or phenyl and $R_4$ denotes hydrogen, an aliphatic or aromatic, araliphatic or alicyclic acyl group with 1-18 C atoms, in which the aromatic part can optionally be substituted by chlorine, $C_1$-$C_4$-alkyl or $C_1$-$C_8$-alkoxy and/or by hydroxyl, and $R_5$ denotes $C_1$-$C_{12}$-alkyl, cyclohexyl, phenyl or benzyl, $R_6$ is hydrogen, hydroxyl, $C_1$-$C_{12}$-alkylamino, cyano or $C_2$-$C_{13}$-alkoxycarbonyl, Y is —O— or

p is 0 or 1, if p is 1 n is 2, 3 or 4 and, if p is 0, n is 0, 1 or 2, m′ m″ in each case independently of one another are 0 or 1, $R_7$ is hydrogen, $C_1$-$C_{12}$-alkyl, $C_2$-$C_7$-alkenyl, cyclohexyl, cyclohexenyl, phenyl, phenyl which is substituted by $C_1$-$C_8$-alkyl, $C_1$-$C_8$-alkoxy and/or hydroxyl, or $C_7$-$C_{13}$-aralkyl, 2-furyl or 2-pyridyl, $R'_1$ and $R_7$ conjointly form branched or unbranched $C_2$-$C_5$-alkylene, $R_8$ is hydrogen or methyl, $R_9$ is hydrogen, $C_1$-$C_{18}$-alkyl or $(M^{+w})/w'$, in which M is a cation with a valency of w and w′ is an integer which is equal to or smaller than w, $R_{10}$ is $C_1$-$C_{18}$-alkyl, q is 1 or 2 and, when q is 1, $R_{11}$ is hydrogen, $C_1$-$C_{18}$-alkyl, $C_2$-$C_4$-alkenyl, $C_3$-$C_{14}$-alkoxyalkyl, cyclohexyl, phenyl, phenyl which is substituted by $C_1$-$C_8$-alkyl or $C_1$-$C_8$-alkoxy, or $C_7$-$C_{13}$-aralkyl or $C_2$-$C_{18}$-acyl and, when q is 2, $R_{11}$ is $C_2$-$C_6$-alkylene or the bis-acyl radical of a $C_2$-$C_{10}$-dicarboxylic acid, r′ and r″ independently of one another have an integral value or are the quotient of two integers between 0 and w, w denoting the valency of the cation mentioned under $R_9$, with the proviso that $w/w' + r''$ equals $q + r'$ when $R_9$ is $(M^{+w})/w'$ and that r′ and r″ are always 0 when $R_9$ is hydrogen or alkyl, L is a monovalent anion of a carboxylic acid with 1-24 C atoms or is the hydroxyl ion, A is an alkali metal cation and s has a value of 0 to 2, Z denotes an amine of the general formula $R_{12}N(R_{13})R_{14}$, in which $R_{12}$ is $C_4$-$C_{12}$-alkyl, $C_3$-$C_{15}$-alkoxyalkyl, $C_7$-$C_8$-aralkyl, $C_5$-$C_8$-cycloalkyl or $C_2$-$C_3$-2-hydroxyalkyl and $R_{13}$ and $R_{14}$ independently of one another denote hydrogen, $C_1$-$C_4$-alkyl or $C_2$-$C_3$-2-hydroxyalkyl, or $R_{12}$ and $R_{13}$, together with the N atom which links them, form a pyrrolidino, morpholino or piperidino radical which is optionally monosubstituted or polysubstituted by methyl, the said piperidino radical optionally carrying amino or $C_1$-$C_{12}$-alkylamino in the 4-position, and t is 0, 1 or 2, with the proviso that t is always 0 when $R_9$ is hydrogen or alkyl.

As $C_1$-$C_4$-alkyl, $R_1$ is branched or, in particular, unbranched alkyl, such as ethyl, n-propyl or n-butyl, but above all methyl. Preferably, $R_1$ is hydrogen. All the substituents $R_1$ are identical.

As $C_1$-$C_4$-alkyl, $R'_1$ and $R''_1$ independently of one another are branched or, in particular, unbranched alkyl, such as ethyl, n-propyl or n-butyl, but above all methyl. Preferably, $R'_1$ and $R''_1$ are hydrogen or methyl.

As $C_1$-$C_{12}$-alkyl, X is, for example, methyl, ethyl, n-propyl, n-butyl, n-pentyl, n-hexyl, n-octyl, n-decyl or n-dodecyl. Preferred alkyl groups are those with 1-8 C atoms, especially those with 1-4 C atoms and above all methyl.

As $C_3$-$C_6$-alkenyl, X is, for example, allyl, 2-butenyl or 2-hexenyl, especially allyl.

As $C_3$-$C_4$-alkinyl, X is, for example, propargyl.

If X denotes $C_2$-$C_{21}$-alkoxyalkyl, the alkyl part can contain 1-3 C atoms and the alkoxy part can consist of 1-18 C atoms, such as in, for example, methoxymethyl, ethoxymethyl, 2-methoxymethyl, 2-ethoxyethyl, 2-n-butoxyethyl, 3-n-butoxyethyl, 2-octoxyethyl or 2-octadecyloxyethyl. Compounds in which X denotes an alkoxyalkyl group with 2-6 C atoms are to be mentioned in particular.

As $C_7$-$C_8$-aralkyl, X is, for example, benzyl or α-phenylethyl.

As an aliphatic acyl group with 1-4 C atoms X is, for example, formyl, acetyl, acryloyl or crotonyl, especially acetyl.

If X is the group —$CH_2COOR_2$, $R_2$, as $C_1$-$C_{12}$-alkyl, denotes, for example, methyl, ethyl, isopropyl, n-butyl, isobutyl, t-butyl, isopentyl, n-octyl, n-decyl or n-dodecyl. $R_2$ is preferably $C_1$-$C_4$-alkyl. As $C_3$-$C_6$-alkenyl, $R_2$ is, for example, allyl, 2-butenyl or 2-hexenyl. As $C_7$-$C_8$-aralkyl, $R_2$ is, for example, benzyl or α-phenylethyl.

If x is the group —$CH_2$—$CH(R_3)$—$OR_4$, $R_3$ denotes hydrogen, methyl or phenyl, especially hydrogen. As an aliphatic, aromatic, alicyclic or araliphatic $C_1$-$C_{18}$-acyl radical which is optionally substituted in the aromatic part by chlorine or $C_1$-$C_4$-alkyl, such as methyl, ethyl, n-propyl or t-butyl, or by $C_1$-$C_8$-alkoxy, such as methoxy, ethoxy, butoxy or octoxy, and/or by hydroxyl, $R_4$ is, for example, acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxbenzoyl, $\beta$-(3,5-di-t-butyl-4-hydroxyphenyl)propionyl, phenylacetyl, cinnamoyl or hexahydrobenzoyl.

If X is the group —COOR$_5$, $R_5$, as $C_1$–$C_{12}$-alkyl, is, for example, methyl, ethyl, isobutyl, n-hexyl, n-octyl, n-decyl or n-dodecyl. Alkyl groups with 1–4 C atoms are preferred as $R_5$. The same applies in the case of $R_5$ in —CONHR$_5$.

As $C_1$–$C_{12}$-alkylamino, $R_6$ is, in particular, $C_1$–$C_{12}$-alkylamino in which alkyl has the meaning indicated for $R_4$, such as methylamino. As $C_2$–$C_{13}$-alkoxycarbonyl, $R_6$ is, in particular, $C_2$–$C_{13}$-alkoxycarbonyl in which the alkyl part has 1–12 C atoms and has the meaning indicated for $R_4$, such as methoxycarbonyl or ethoxycarbonyl.

As $C_1$–$C_{12}$-alkyl, $R_7$ is, in particular, propyl, isopropyl, n-butyl, n-hexyl or n-undecyl. As $C_2$–$C_7$-alkenyl, $R_7$ is, for example, vinyl, allyl or methallyl. As phenyl which is substituted by $C_1$–$C_8$-alkyl, $C_1$–$C_8$-alkoxy and/or hydroxyl, $R_7$ is, for example, a phenyl radical of this type in which alkyl has the meaning indicated for X, such as methyl or tert.-butyl, and in which alkoxy is, for example, methoxy or ethoxy, such as 3,5-di-tert.butyl-4-hydroxy-phenyl. As $C_7$–$C_{13}$-aralkyl, $R_7$ is, in particular, a $C_7$–$C_{13}$-aralkyl such as has been indicated for X, such as benzyl.

If $R'_1$ and $R_7$ conjointly form a branched or unbranched $C_2$–$C_5$-alkylene, the latter is ethylene, methylethylene, 1-methylpropylene or 1,3-dimethylpropylene, but especially n-propylene or 2,2-dimethyopropylene.

As $C_1$–$C_{18}$-alkyl, $R_9$, $R_{10}$ and $R_{11}$ in particular denote methyl, ethyl or n-butyl.

A cation which has a valency of w is, for example, a metal ion, especially a metal ion of the series comprising $Mg^{+2}$, $Ca^{+2}$, $Sr^{+2}$, $Ba^{+2}$, $Zn^{+2}$, $Cd^{+2}$, $Al^{+3}$, $Cu^{+2}$, $Sn^{+2}$, $Cr^{+3}$, $Co^{+2}$ and especially $Ni^{+2}$, as also an oxo complex of metal ions, especially $VO^{+2}$ and $MoO_2^{+2}$, or a tin-alkyl ion of the formula $(R'_9)_2Sn^{+2}$, in which $R'_9$ denotes a $C_1$–$C_8$-alkyl, but especially ethyl, n-propyl, n-butyl and n-octyl.

As $C_2$–$C_4$-alkenyl, $R_{11}$ is, in particular, vinyl, allyl or methallyl. As $C_3$–$C_{14}$-alkoxyalkyl, $R_{11}$ is branched or, in particular, straight-chain alkoxyalkyl with, in particular, 3–8 C atoms, such as 2-methoxyethyl, 2-ethoxyethyl, 3-methoxypropyl or 3-ethoxypropyl. If $R_{11}$ is phenyl which is substituted by $C_1$–$C_8$-alkyl or $C_1$–$C_8$-alkoxy, these substituents in particular contain 1–4 C atoms, such as methyl or methoxy. As $C_7$–$C_{13}$-aralkyl, $R_{11}$ is, in particular, phenethyl or, above all, benzyl. As $C_2$–$C_{18}$-acyl, $R_{11}$ in particular has the meaning indicated for $R_4$ and above all the meanings indicated under $R_4$ by way of example. As $C_2$–$C_6$-alkylene, $R_{11}$ is branched or, in particular, straight-chain alkylene, such as di-, tri-, tetra-, penta- or hexa-methylene. As the bis-acyl radical of a $C_2$–$C_6$-dicarboxylic acid, $R_{11}$ is, in particular, a bis-acyl radical of an alkene-dicarboxylic acid or, in particular, of an alkane-dicarboxylic acid, such as oxalic acid, malonic acid, succinic acid, glutaric acid, adipic acid, fumaric acid or maleic acid.

As $C_4$–$C_{12}$-alkyl, $R_{12}$ is, for example, n-butyl, t-butyl, n-pentyl, n-hexyl, 2-ethylhexyl, t-octyl, n-decyl or n-dodecyl. $C_4$–$C_8$-alkyl groups, and especially n-butyl and 2-ethylhexyl, are preferred.

As $C_3$–$C_{15}$-alkoxyalkyl, $R_{12}$ is, for example, methoxypropyl, ethoxy-n-butyl, methoxy-n-octyl, ethoxy-t-octyl or t-butoxy-decyl. $C_4$–$C_8$-alkoxyalkyl groups, and especially methoxypropyl and ethoxyhexyl, are preferred.

As $C_7$–$C_8$-aralkyl, $R_{12}$ is phenethyl and especially benzyl.

As $C_5$–$C_8$-cycloalkyl, $R_{12}$ is, for example, cyclopentyl, cycloheptyl, cyclooctyl and especially cyclohexyl.

As $C_2$–$C_3$-2-hydroxyalkyl, $R_{12}$ is 2-hydroxy-n-propyl and especially 2-hydroxyethyl.

As $C_1$–$C_4$-alkyl, $R_{13}$ and $R_{14}$ have the same meaning as $R_1$ and as $C_2$–$C_3$-2-hydroxyalkyl they have the same meaning as the corresponding $R_{12}$. However, $R_{13}$ and $R_{14}$ are preferably hydrogen.

If $R_{12}$ and $R_{13}$, conjointly with the N atom which links them, form pyrrolidino, morpholino or piperidino, these are unsubstituted pyrrolidino, morpholino or piperidino or 2,2,6,6-tetramethylpiperidino, but especially 2,2,6,6-tetramethylpiperidino substituted in the 4-position by amino or $C_1$–$C_{12}$-n-alkylamino.

According to the definition, L is a monovalent anion of a carboxylic acid or a hydroxyl ion. Possible carboxylic acids are both aliphatic or cycloaliphatic and also aromatic or araliphatic carboxylic acids. They can be monocarboxylic acids or partial esters of polycarboxylic acids. The carboxylic acids can be unsaturated and carry substitutents such as, for example, ether groups or ester groups. Examples of suitable carboxylic acids are: acetic acid, gycollic acid, monohexyl diglycollate, lactic acid, 2-ethylcaproic acid, monobutyl maleate, monododecyl thiodiglycollate, lauric acid, oleic acid, stearic acid, cyclohexanecarboxylic acid, monooctyl hexahydrophthalate, monobutyl phthalate, benzoic acid, 4-hydroxy-3,5-di-tert.-butyl-benzoic acid, salicylic acid, salicylic acid propyl ether, phenylacetic acid or 2-naphthylpropionic acid.

When A denotes an alkali metal cation it can be $Na^+$, $K^+$, $Li^+$, $Rb^+$ or $Cs^+$.

The water content expressed by $(H_2O)_s$ in formula I is usually due to a water content in the metal salts used as the starting material. Depending on the conditions for isolation and drying, some of this water can arrive as a ligand of the central atom $M^{+w}$ but some of it can also be incorporated in the end product as water of crystallisation. Therefore, the coefficient s can have the value either of an integer or of a fractional number within the indicated limits.

Compounds of the formula I in which $R_1$, $R'_1$ and $R''_1$ are hydrogen or methyl, X is hydrogen, oxyl, $C_1$–$C_8$-alkyl, $C_3$–$C_4$-alkenyl or -alkinyl, $C_2$–$C_6$-alkoxyalkyl, $C_7$–$C_8$-aralkyl, acetyl, acryloyl or crotonoyl, or denotes one of the groups —CH$_2$—COOR$_2$, —CH$_2$—CH(R$_3$)—OR$_4$ or —CONHR$_5$, in which $R_2$ is $C_1$–$C_4$-alkyl, $C_3$–$C_4$-alkenyl, phenyl, $C_7$–$C_8$-aralkyl or cyclohexyl and $R_3$ is hydrogen, methyl or phenyl and $R_4$ denotes hydrogen or an aliphatic, aromatic, alicyclic or araliphatic acyl group with 1–18 C atoms, in which the aromatic part can optionally be substituted by chlorine, $C_1$–$C_4$-alkyl, $C_1$–$C_8$-alkoxy and/or hydroxyl, and $R_5$ is $C_1$–$C_{12}$-alkyl, $R_6$ is hydrogen, hydroxyl or $C_1$–$C_{12}$-alkylamino, Y is —O— or —NH—, p is 0 or 1 and, when p is 0, n is 0, 1 or 2 and, when p is 1, n is 2 or 3, m' and m" independently of one another are 0 or 1, $R_7$ is hydrogen, $C_1$–$C_{11}$-alkyl, $C_2$–$C_4$-alkenyl, cyclohexyl, cyclohexenyl, phenyl or phenyl which is substituted by $C_1$–$C_4$-alkyl, $C_1$–$C_4$-alkoxy and/or hydroxyl or is $C_7$–$C_8$-aralkyl, $R'_1$ and $R_7$ conjointly form n-propylene or 2,2-dimethylpropylene, $R_8$ is hydrogen, $R_9$ is hydrogen, $C_1$–$C_8$-alkyl or $Mg^{+2}/w'$, $Ca^{+2}/w'$, $Sr^{+2}/w'$, $Ba^{+2}/w'$, $Zn^{+2}/w'$, $Cd^{+2}/w'$, $Al^{+3}/w'$, $Sn^{+2}/w'$, $VO^{+2}/w'$, $Cr^{+3}/w'$, $Co^{+2}/w'$, $Ni^{+2}/w'$, (n-$C_4H_9)_2Sn^{+2}/w'$ or $MoO_2^{+2}/w'$, in which $w'$ is an integer which is identical to or smaller than the charge on these cations, $R_{10}$ is $C_1$–$C_8$-alkyl, q is 1, $R_{11}$ is hydrogen or $C_1$–$C_8$-alkyl, $r'$ and $r''$ independently of one another have an integral value or are the quotients of two integers between 0 and w, w denoting the valency of the cation indicated under $R_9$, with the proviso that $w/w' + r''$ equals $q + r'$ when $R_9$ is $(M^{+w})/w'$ and that $r'$ and $r''$ are always 0 when $R_9$ is hydrogen or alkyl, L is a monovalent anion of an aliphatic carboxylic acid with 2–18 C atoms or of an aromatic carboxylic acid with 7–18 C atoms or is a hydroxyl ion, A is a sodium cation or potassium cation and s has a value of 0 to 2, Z denotes an amine of the general formula $R_{12}N(R_{13})R_{14}$, in which $R_{12}$ is $C_4$–$C_8$-alkyl or $C_2$–$C_3$-2-hydroxyalkyl and $R_{13}$ and $R_{14}$ independently of one another are hydrogen, $C_4$–$C_8$-alkyl or $C_2$–$C_3$-2-hydroxyalkyl, or $R_{12}$ and $R_{13}$, together with the N atom which links them, form a piperidine radical which is polysubstitued by methyl and optionally substituted in the 4-position by amino or $C_1$–$C_8$-n-alkylamino, and t is 0, 1 or 2, with the proviso that t is always 0 when $R_9$ is hydrogen or alkyl, are preferred.

Compounds of the formula I in which $R_1$, $R'_1$ and $R'_1$ are hydrogen or methyl, X is hydrogen, $C_1$–$C_4$-alkyl, allyl, benzyl, $C_2$–$C_6$-alkoxyalkyl, acetyl, acryloyl or crotonoyl or is one of the groups $-CH_2-COOR_2$, $-CH_2-CH(R_3)-OR_4$ or $-CONHR_5$, in which $R_2$ is $C_1$–$C_4$-alkyl, $R_3$ is hydrogen or methyl, $R_4$ denotes hydrogen and $R_5$ is $C_1$–$C_4$-alkyl, $R_6$ is hydrogen or hydroxyl, Y is $-O-$ or $-NH-$, p is 0 or 1 and, when p is 0, n is 0, 1 or 2 and, when p is one, n is 2 or 3, $m'$ and $m''$ independently of one another are 0 or 1, $R_7$ is hydrogen, $C_1$–$C_7$-alkyl, phenyl or $C_7$–$C_8$-aralkyl, $R'_1$ and $R_7$ conjointly form n-propylene or 2,2-dimethylpropylene, $R_8$ is hydrogen, $R_9$ is hydrogen, $C_1$–$C_4$-alkyl or $Zn^{+2}/w'$, $Mg^{+2}/w'$, $Ca^{+2}/w'$, $Al^{+3}/w'$, $Co^{+2}/w'$ or $Ni^{+2}/w'$, $w'$ being an integer which is identical to or smaller than the charge on the cations, $R_{10}$ is $C_1$–$C_8$-alkyl, q is 1, $R_{11}$ is hydrogen or $C_1$–$C_4$-alkyl, $r'$ and $r''$ independently of one another have an integer value or are a quotient of two integers between 0 and w, w denoting the valency of the cation indicated under $R_9$, with the proviso that $w/w' + r''$ equals $q + r'$ when $R_9$ is $(M^{+w})/w'$ and that $r'$ and $r''$ are always 0 when $R_9$ is hydrogen or alkyl, L is a monovalent anion of an aliphatic carboxylic acid with 2–18 C atoms or is a hydroxyl ion, A is a sodium cation or potassium cation, s has a value of 0 to 2 and Z denotes an amine of the general formula $R_{12}N(R_{13})R_{14}$, in which $R_{12}$ is $C_4$–$C_8$-alkyl or 2-hydroxyethyl and $R_{13}$ and $R_{12}$ independently of one another are hydrogen, $C_4$–$C_8$-alkyl or 2-hydroxyethyl, or $R_{12}$ and $R_{14}$, together with the N atom which links them, form 4-n-octylamino-2,2,6,6-tetramethylpiperidine, and t is 0, 1 or 2, with the proviso that t is always 0 when $R_9$ is hydrogen or alkyl, are particularly preferred.

Compounds of the formula I in which $R_1$ is hydrogen, $R'_1$ and $R''_1$ are hydrogen or methyl, X is hydrogen, methyl, allyl, benzyl or acetyl, $R_6$ is hydrogen or hydroxyl, p is 0 or 1 and, when p is 0, n is 0, 1 or 2 and, when p is one, n is 3, $m'$ and $m''$ independently of one another are 0 or 1, $R_7$ is hydrogen, $C_1$–$C_6$-alkyl or phenyl, $R'_1$ and $R_7$ conjointly form n-propylene or 2,2-dimethylpropylene, $R_8$ is hydrogen, $R_9$ is hydrogen, methyl, ethyl or $Zn^{+2}/w'$, $Mg^{+2}/w'$, $Al^{+3}/w'$, $Co^{+2}/w'$ or $Ni^{+2}/w'$, $w'$ being an integer which is equal to or smaller than the charge on the cations, $R_{10}$ is $C_1$–$C_4$-alkyl, q is 1, $R_{11}$ is hydrogen, $r'$ and $r''$ independently of one another have an integral value or are the quotient of two integers between 0 and w, w denoting the valency of the cation indicated under $R_9$, with the proviso that $w/w' + r''$ equals $q + r'$ when $R_9$ is $(M+w)w'$ and $r'$ and $r''$ are always 0 when $R_9$ is hydrogen or alkyl, L is a monovalent anion of an alkanecarboxylic acid with 2–12 C atoms or is a hydroxyl ion, A is a sodium cation, s has a value of 0 to 2 and Z denotes an amine of the general formula $R_{12}N(R_{13})R_{14}$, in which $R_{12}$ is $C_4$–$C_8$-alkyl, $R_{13}$ is n-butyl and $R_{14}$ is hydrogen, and t is 0 or 1 or 2, with the proviso that t is always 0 when $R_9$ is hydrogen or alkyl, are very particularly preferred.

In addition to the compounds mentioned in the examples, the preferred compounds above, in which $R_1$ is hydrogen, are to be singled out in particular.

The compounds of the formula I can be manufactured by various methods which consist of several individual steps in various sequences. The individual steps consist of reactions which are in themselves known.

Thus, the aminophosphonic acid esters of the formula I (in which $R_9$ and $R_{10}$ represent alkyl radicals) can be manufactured by one of the following processes, which are in themselves known:

α-Aminophosphonic acid derivatives: these compounds can be manufactured by reacting a diester of phosphorous acid simultaneously with an aldehyde or ketone and with a primary or secondary amine, the amino group which participates in the reaction representing a constituent of an organic radical which is bonded, in the 4-position, to a 2,2,6,6-tetraalkylated piperidine nucleus, which is optionally alkylated in the 3-position; alternatively, the amino group can be located direct in the 4-position on the said nucleus. These reactions can either be carried out in one step or can be effected by an addition reaction of the diester of phosphorous acid with the azomethine compound formed, in a first stage, from the amine and the carbonyl compound (E. K. Fields, J. Am. Chem. Soc. 74, 1,528 (1952); and also U.S. Pat. No. 2,635,122).

β-Aminophosphonic acid derivatives: these compounds can be prepared by reacting a 62-aminophosphonic acid ester (which can be manufactured, for example, according to German Offenlegungsschrift No. 2,358,835) with a ketone (especially 2,2,6,6-tetramethyl-piperidin-4-one), the azomethine double bond which forms simultaneously being reduced by the method of "reductive alkylation" (see Houben-Weyl, volume 11/1, pages 619 et seq., and 627 et seq.).

γ-Aminophosphonic acid derivatives: γ-aminophosphonic acid esters can be manufactured from corresponding γ-oxophosphonic acid esters (which are obtained from α,β-unsaturated ketones: compare Houben-Weyl, volume 12/1, 465) by aminating hydrogenation (compare German Offenlegungsschrift No. 2,358,836). These aminophosphonates can be prepared by the abovementioned method of "reductive alkylation" using a 2,2,6,6-tetraalkylpiperidin-4-one, which is optionally alkylated in the 3-position, or by means of a keto group or aldehyde group which is a constituent of a side chain in the 4-position of a 2,2,6,6-tetraalkylated piperidine which is optionally alkylated in the 3-position. The γ-oxophosphonic acid diesters which have been mentioned can, however, also be prepared direct by the latter method, by reaction with primary amines which contain a 2,2,6,6-tetraalkylated 4-piperidyl radical.

The aminophosphonic acid half-esters of the formula I ($R_9$ = H) can be obtained from the corresponding diesters by partial hydrolysis (compare Houben-Weyl, volume 12/1, page 410; V. Jagodic, Chem. Ber. 93, 2,308 (1960)).

The metal complexes included under the formula I are manufactured in a manner which is in itself known, for example by dissolving the aminophosphonic acid half-ester in a nonaqueous solvent, preferably a lower alcohol (especially ethanol) and neutralising the solution with the equivalent amount of an alkali metal alcoholate. The number of mols of a dissolved metal salt which are required to bring the molar ratio between the metal ion, which has a valency of w, and the phosphonic acid half-ester groups of the ligand molecule to 1:w are then added slowly. The solvent which can be used for the metal salt is, above all, that used initially or a solvent miscible with this first solvent. The reaction mixture is then stirred for 1 hour at a temperature of between 30° and 100° C. Metal salts which can be used are, preferably, those which have anions which give sparingly soluble precipitates with the alkali metal ions in the chosen solvents. Precipitation usually takes place when the metal salt is added or on subsequent stirring or heating of the reaction mixture. In these cases, the alkali metal salts can be separated off by filtration. Otherwise, they can frequently be separated off by evaporating the solvent or by extracting the metal compound with a non-polar solvent. Metal salts which can be used are, in particular, chlorides, such as nickel chloride, cobalt-II chloride or dibutyl-tin dichloride. If the salts used are not anhydrous or if the phosphonic acid half-ester isolated as an inner salt contains water of hydration, this water can be incorporated in the complexes which form and cannot be removed therefrom by the action of heat. If a salt of a carboxylic acid (for example the nickel salt of 2-ethylcaproic acid) is used as the metal salt, the carboxylate ion can frequently not be separated off, or can be only partially separated off, as the alkali metal salt because it is incorporated in the complex as a further ligand anion (L in formula I), in addition to the aminophosphonic acid half-ester.

Metal alkoxides (such as, for example, aluminium triisopropylate) or metal oxides (such as magnesium oxide) can also be used, in place of inorganic metal salts and metal carboxylates, as reactants for the formation of metal complexes. In these cases, the neutralisation of the aminophosphonic acid half-ester with an alkali metal alcoholate is dispensed with. However, when metal oxides are used the reaction mixture must be heated to temperatures of up to 135° for a relatively long time.

If the metal complexes of the formula I contain an amine (Z) as further ligand, this amine can already be added during the preparation of the neutralised phosphonic acid half-ester solution; alternatively, the metal complex obtained in the manner described above can be dissolved in a solvent containing the amine and the solvent can then be removed again by evaporating off.

When the metal complexes of the formula I are manufactured following the procedure described, mixtures of different complexes of the formula I are frequently formed. These mixtures can be used as effective stabilisers, in the same way as the homogeneous compounds of this formula.

The starting materials are known or, if they are new, can be manufactured by methods which are in themselves known and analogously to known compounds. Thus, for example, 4-aminopiperidine derivatives are important starting materials which can be manufactured by the processes described in German Offenlegungsschrift No. 2,040,975 or German Offenlegungsschrift No. 2,349,962. Those piperdine derivatives which are substituted on the 4-amino group by an alkylamino group can be manufactured analogously by starting from a piperidine-4-one derivative and reacting this with a monoalkylated diamine.

The piperidine derivatives which contain an alkoxyamino group (especially an hydroxypropylamino group) in the 4-position are manufactured from the corresponding 4-hydroxy-piperidine derivatives, the latter being subjected, according to a method which is in itself known, to an addition reaction with acrylonitrile and the cyano group subsequently being hydrogenated to the corresponding primary amine. Further important starting materials for the manufacture of compounds according to formula I are those compounds which carry both a cyano group and a hydroxy group (cyanohydrins), or both a cyano group and an amino group, in the 4-position of the piperidine ring. The manufacture of these compounds has been described in U.S. Pat. No. 3,513,170. The corresponding 4-methylamino derivatives are then obtained in a known manner by hydrogenation of these nitriles. α-Aminocarboxylic acid esters, the α-carbon atom of which is in the 4-position in the piperidine derivatives which can be used, are also starting materials for the manufacture of the claimed compounds of the formula I.

The free acids can be manufactured from the corresponding piperidin-4-one derivatives by the method of H. T. Bucherer (J. Prakt. Chem. 140, 291 (1934)) via hydantoins, as intermediate products, and subsequent alkaline saponification. Conversion into the corresponding esters is effected in a manner which is in itself known with the aid of an acid catalyst.

The piperidin-4-one derivatives which are substituted on the nitrogen in the 1-position can be obtained, as described in British Pat. No. 1,337,600, by protecting the keto group by converting it into a ketal. After the substituent has been introduced into the 1-position by the customary methods, the protective group is split off again in a known manner.

According to the present invention, the compounds of the formula I can be used as stabilisers for plastics, to protect them against damage due to the action of oxygen, heat and light. Examples of such plastics are the polymers specified in German Offenlegungsschrift No. 2,456,864 (pages 12–14).

The stabilisation of polyolefines, styrene polymers and polyamides and of polyurethanes is of particular importance and the compounds of the formula I are outstandingly suitable for this. Examples of such polymers are high-density polyethylene and low-density polyethylene, polypropylene, ethylene/propylene copolymers, polystyrene, styrene/butadiene/acrylonitrile copolymers, mixtures of polyolefines or of styrene polymers and polyurethanes based on polyethers or polyesters, in the form of lacquers, filaments, films, elastomers or foams.

The stabilisers are added to the plastics in a concentration of 0.01 to 5% by weight, calculated relative to the material to be stabilised. Preferably, 0.03 to 1.5, and particularly preferentially 0.15 to 0.6, % by weight of the compounds, calculated relative to the material to be stabilised, are incorporated into the latter.

Incorporation can be effected after polymerisation, for example by mixing the compounds, and optionally further additives, into the melt by the methods customary in the art, before or during shaping, or by applying the dissolved or dispersed compounds to the polymer, if necessary with subsequent evaporation of the solvent.

The new compounds can also be added to the plastics to be stabilised in the form of a master batch which contains these compounds, for example in a concentration of 2.5 to 25% by weight.

In the case of crosslinked polyethylene, the compounds are added prior to crosslinking.

In addition to the compounds of the formula I, yet further known stabilisers can also be added to the plastics. These stabilisers can be, for example, antioxidants, light stabilisers or metal deactivators, or also costabilisers, such as, for example, those of the phosphorous acid ester type. Furthermore, other additives customary in plastics technology, such as, for example, flameproofing agents, antistatic agents, plasticisers, lubricants, blowing agents, pigments, reinforcing materials or fillers, can be added.

The invention therefore also relates to plastics stabilised by the addition of 0.01 to 5% by weight of a compound of the formula I, which plastics optionally can contain yet further known and customary additives. The plastics stabilised in this way can be used in very diverse forms, for example as films, fibres, tapes or profiles, or as binders for lacquers, adhesives or putties.

Manufacture and use of the compounds according to the invention are described in more detail in the examples which follow. In these examples, parts by weight and the temperatures are given in degrees Centigrade.

EXAMPLE 1

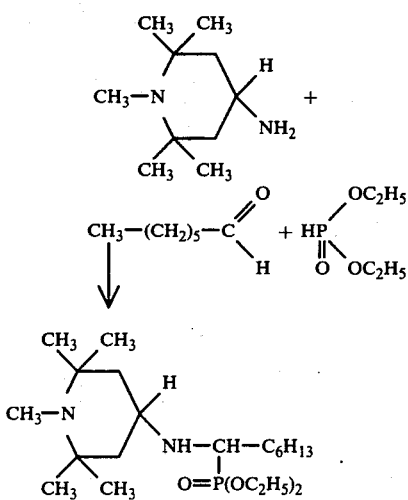

26.6 g (0.10 mol) of 1,2,2,6,6-pentamethyl-4-heptylidene-aminopiperidine (boiling point 94–96°/0.05 mm Hg), obtained by subjecting an equimolar mixture of 1,2,2,6,6-pentamethyl-4-aminopiperidine and 1-heptanal to a condensation reaction at 0°, and 13.8 g (0.10 mol) of diethyl phosphite and 0.35 g of sodium ethylate (dissolved in 4.5 ml of ethanol) are heated to 95° for 4½ hours. The reaction product is taken up in ether and the ether is washed with water, dried over sodium sulphate and evaporated. In this way diethyl-1-[(1,2,2,6,6-pentamethyl-4-piperidyl)-amino]-n-heptyl-phosphonate is obtained as a pale yellow oil Analysis: calculated C 62.4%, H 11.2%, N 6.9%, P 7.6%; found: C 61.8%, H 11.5%, N 6.9%, P 7.3%.

EXAMPLE 2

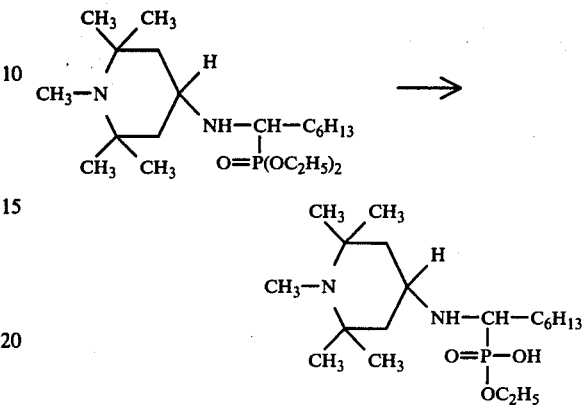

40.5 g (0.10 mol) of the diethyl 1-[(1,2,2,6,6-pentamethyl-4-piperidyl)-amino]-n-heptyl-phosphonate from Example 1, in a solution which contains 5.61 g (0.10 mol) of potassium hydroxide in 100 ml of ethanol, are boiled under reflux for 45 hours. Hydrochloric acid is now added to the reaction mixture in an amount such that a sample of the reaction mixture diluted with water in a volume ratio of 1:1 has a pH value of 7.3, and the neutralised solution is evaporated to dryness and the residue is freed, by extraction with acetone, from potassium chloride which has formed. When this extract is concentrated, a precipitate separates out and this can be recrystallised from a mixture of acetone and ethanol in a volume ratio 7:3.

In this way ethyl-1-[(1,2,2,6,6-pentamethyl-4-piperidyl)-amino]-n-heptyl-phosphonate, which melts at 219°, is obtained.

Analysis: calculated: C 60.61% H 10.98% N 7.44%; found: C 60.35% H 10.8% N 7.5%.

EXAMPLE 3

18.8 g (0.05 mol) of the ethyl-1-[(1,2,2,6,6-pentamethyl-4-piperidyl)-amino]-n-heptyl-phosphonate from Example 2 are dissolved in 400 ml of ethanol with the addition of 3.40 g (0.05 mol) of sodium ethylate. A solution of 4.14 g (0.025 mol) of nickel chloride dihydrate in 100 ml of ethanol is added dropwise to this solution at 25° and the mixture is stirred at 25° for 3 hours. The sodium chloride which has precipitated out is now filtered off, the solvent is evaporated off and the residue is extracted with ether. After volatilising the solvent, the extract is dried for 10 hours at a temperature of 60° and under a pressure of 11 mm Hg. Ni-di-{ethyl-1-[(1,2,2,6,6-pentamethyl-4-piperidyl)-amino]-n-heptyl-phosphonate}-monohydrate is obtained as a green-yellow solid product. It is soluble in hexane at room temperature.

Analysis: calculated: C 55.13%, H 9.99%, N 6.77%, P 7.48%, Ni 7.09%; found: C 55.10%, H 10.1%, N 6.8%, P 7.7%, Ni 6.9%.

EXAMPLE 4

18.8 g (0.05 mol) of the ethyl-1-[(1,2,2,6,6-pentamethyl-4-piperidyl)-amino]-n-heptyl-phosphonate from Example 2 are dissolved in 200 ml of ethanol with the addition of 3.40 g (0.05 mol) of sodium ethylate.

6.23 g (0.025 mol) of cobalt acetate tetrahydrate, dissolved in 50 ml of ethanol, are added dropwise to this solution, the reaction mixture is heated under reflux for ½ hour and the solvent is then distilled off. The residue is extracted with toluene at the boil and, after an insoluble precipitate has been filtered off and the solution has been evaporated again, the residue is extracted with ether. If the ether is evaporated off and the residue is dried at a temperature of 30° and under a pressure of 11 mm Hg, Co-di-{ethyl-1-[(1,2,2,6,6-pentamethyl-4-piperidyl)-amino]-n-heptyl-phosphonate}-monohydrate is obtained as a solid blue product. It is soluble in hexane at room temperature.

Analysis: calculated: C 55.12%, H 9.98%, N 6.77%, P 7.48%, Co 7.12%; found: C 55.3%, H 10.0%, N 6.5%, P 7.3%, Co 6.6%.

EXAMPLE 5

18.8 g (0.05 mol) of the ethyl-1-[(1,2,2,6,6-pentamethyl-4-piperidyl)-amino]-n-heptyl-phosphonate from Example 2 are dissolved in 200 ml of ethanol with the addition of 3.40 g (0.05 mol) of sodium ethylate. 5.49 g (0.025 mol) of zinc acetate dihydrate, dissolved in 200 ml of ethanol, are added dropwise to this solution at 25°. After the reaction mixture has been heated under reflux for ¼ hour, the clear solution is evaporated and the residue is extracted with ether. The extract obtained after evaporating off the ether is dried at a temperature of 30° under a pressure of 11 mm Hg. Zn di-{ethyl-1-[(1,2,2,6,6-pentamethyl-4-piperidyl)-amino]-n-heptyl-phosphonate}-sodium acetate is obtained as a white solid product which is soluble in hexane at room temperature.

Analysis: calculated: C 53.47%, H 9.31%, N 6.24%, P 6.89%, Zn 7.27%; found: C 53.2%, H 9.4%, N 6.1%, P 6.8%, Zn 7.3%.

EXAMPLE 6

22.6 g (0.06 mol) of the ethyl-1-[(1,2,2,6,6-pentamethyl-4-piperidyl)-amino]-n-heptyl-phosphonate from Example 2 are heated in 200 ml of absolute ethanol with 4.08 g (0.02 mol) of aluminium isopropylate for one hour under reflux. The resulting solution is evaporated and the residue is dried at a temperature of 30° under a pressure of 11 mm Hg. In this way, Al tri-{ethyl-1-[(1,2,2,6,6-pentamethyl-4-piperidyl)-amino]-n-heptyl-phosphonate} is obtained as a white solid product which is soluble in hexane at room temperature. Analysis: calculated: C 59.35%, H 10.49%, N 7.20%, P 8.06%, Al 2.34%: found: C 58.2%, H 10.7%, N 7.2%, P 7.9%, Al 2.4%.

EXAMPLE 7

20.4 g (0.05 mol) of ethyl-α-[(2,2,6,6-tetramethyl-4-piperidyl)-amino]-benzyl-phosphonate in the form of the trihydrate are dissolved in 600 ml of ethanol with the addition of 3.40 g (0.05 mol) of sodium ethylate and 8.63 g (0.025 mol) of the nickel-II salt of 2-ethylcaproic acid and 1.83 g (0.025 mol) of n-butylamine are added to this solution. A beige precipitate which is then deposited is filtered off, the filtrate is evaporated to dryness and the residue is extracted with methylene chloride at 25°. The filtrate is again evaporated and the residue is extracted with toluene at the boil. After evaporating the extract and drying the residue at 80° and under a pressure of 11 mm Hg, a pale green solid product which is soluble in hot ligroin is obtained. Elementary analysis gives the following results:

Analysis: found: C 59.0% H 9.2% N 5.5% P 5.3% Ni 6.2%.

On the basis of this composition it must be assumed that the nickel-II complex contains the 2-ethylcaproate anion and n-butylamine as further ligands, in addition to the α-aminophosphonate anion of the abovementioned acid, or that the product is made up of mixtures of nickel-II complexes of the formula I.

The ethyl-α-[(2,2,6,6-tetramethyl-4-piperidyl)-amino]-n-benzyl-phosphonate used as the starting material was obtained by alkaline saponification of the corresponding diester. This diester is prepared by an addition reaction of diethyl phosphite with the imine which is obtained by a condensation reaction of 2,2,6,6-tetramethyl-4-amino-piperidine and benzaldehyde.

EXAMPLE 8

77.6 g (0.5 mol) of triacetonamine and 90.6 g (0.5 mol) of diethyl β-aminoethanephosphonate are dissolved in 1,500 ml of ethanol and hydrogenated, with the addition of 4 g of platinum-on-charcoal (containing 5% of platinum) at 25° in an autoclave under a slight excess pressure until the absorption of hydrogen has ceased. The catalyst is filtered off and the filtrate is distilled. In this way, diethyl-2-[(2,2,6,6-tetramethyl-4-piperidyl)-amino]-ethylphosphonate is obtained as a fraction which boils at a temperature of 145° under a pressure of 0.8 mm Hg.

Analysis: calculated: C 56.23%, H 10.38%, N 8.75%; found: C 56.5%, H 10.65%, N 8.7%.

From this phosphonic acid half-ester is obtained the corresponding half-ester, O-ethyl-2-[(2,2,6,6-tetramethyl-4-piperidyl)-amino]-ethylphosphonic acid, by saponification in the equimolecular amount of an ethanolic potassium hydroxide solution. After refluxing for 60 hours, there is added 20% of water, and the pH value of the solution is reduced to pH 8.9 by the addition of hydrochloric acid. The solvent is subsequently evaporated off, and the residue is extracted firstly with acetone and then with ethanol. The ethanolic extract is concentrated by evaporation, and recrystallised from a mixture of acetone and ethanol to give a white precipitate. The half-ester of the aforementioned composition, obtained in this manner, contains 10.53% of P (cal. 10.60%) and 9.38% of N (cal. 9.58%). Acidimetric titration gives the equivalent weight of 293 (cal. 292).

EXAMPLE 9

77.6 g (0.5 mol) of triacetonamine are mixed slowly with 97.6 g (0.5 mol) of diethyl-γ-aminopropanephosphonate in 250 ml of ether, whilst cooling. After adding 100 g of a molecular sieve (5 Å), the mixture is stirred at room temperature for 24 hours, the molecular sieve is filtered off, the ether is evaporated off and the residue is dissolved in 1,000 ml of ethanol. This solution is hydrogenated at 25° in an autoclave, with the addition of 14 g of platinum-on-charcoal (containing 5% of platinum), under a slight excess pressure until the absorption of hydrogen has ceased. The catalyst is filtered off and the filtrate is distilled.

In this way, diethyl-3-[(2,2,6,6-tetramethyl-4-piperidyl)-amino]-n-propyl-phosphonate is obtained as a fraction which boils at a temperature of 155° under a pressure of 0.8 mm Hg.

Analysis: calculated: C 57.65%, H 10.51%, N 8.41%, P 9.31%; found: C 57.1%, H 10.6%, N 8.4%, P 9.3%.

EXAMPLE 10

21.0 g (0.10 mol) of 2,2,6,6-tetramethyl-4-(isobutylideneamino)-piperidine (b.p. 42°–43°/0.05 mm Hg), obtained by condensation of an equimolecular mixture of 2,2,6,6-tetramethyl-4-aminopiperidine with isobutyraldehyde at 0°, and 13.8 g (0.10 mol) of diethyl phosphite and 0.02 g of sodium ethylate (dissolved in 0.3 ml of ethanol) are heated for 3½ hours at 90°. The reaction product is dissolved in ether, washed with a saturated sodium chloride solution, dried over potassium carbonate and, after removal of the solvent by distillation, distilled (b.p. 133°/0.4 mm Hg). Diethyl-1-[(2,2,6,6-tetramethyl-4-piperidyl)-amino]-isobutyl-phosphonate is obtained in this manner.

Analysis: calculated: C 58.59%, H 10.70%, N 8.04%, P 8.89%; found: C 58.44%, H 10.62%, N 8.04%, P 9.04%.

EXAMPLE 11

27.4 g (0.10 mol) of 2,2,6,6-tetramethyl-4-hydroxy-4-methylbenzylideneamino-piperidine (m.p. 84°), obtained by boiling an equimolecular solution of 2,2,6,6-tetramethyl-4-hydroxy-4-methylamino-piperidine and benzaldehyde in toluene on a water separator, are dissolved in 180 ml of ethanol; 0.2 g of sodium ethylate is added, and refluxing is maintained for 6 hours. The solvent is then evaporated off, and the residue is taken up in ether and washed with water. The ether phase, dried over sodium sulphate, is concentrated by evaporation, and the residue is recrystallised from hexane. In this manner is obtained diethyl-1-[(2,2,6,6-tetramethyl-4-hydroxy-4-piperidyl)-methylamino]-benzylphosphonate in the form of a white crystalline mass melting at 91°.

Analysis: calculated: C 61.15%, H 9.04%, N 6.79%, P 7.51%; found: C 61.48%, H 9.02%, N 6.88%, P 7.30%.

EXAMPLE 12

31.0 g (0.21 mol) of triacetonamine and 33.4 g (0.20 mol) of diethyl aminomethylphosphonate are dissolved in 500 ml of ethanol, and the solution is hydrogenated, with the addition of 3 g of platinum-on-charcoal (containing 5% of platinum) and 3 drops of concentrated sulphuric acid, under a slight excess pressure until the absorption of hydrogen has ceased. The catalyst is filtered off and the filtrate is distilled. In this way is obtained diethyl (2,2,6,6-tetramethyl-4-piperidyl)-aminomethylphosphonate as a fine fraction which boils, under a pressure of 0.35 mm Hg, at a temperature of 130°.

Analysis: calculated: C 54.88%, H 10.20%, N 9.14%, P 10.11%; found: C 54.27%, H 9.94%, N 9.05%, P 10.13%.

From this phosphonic acid half-ester is obtained the potassium salt of the respective half-ester, namely the potassium salt of O-ethyl-(2,2,6,6-tetramethyl-4-piperidyl)-aminomethylphosphonic acid, by refluxing for 36 hours with the equimolecular amount of potassium hydroxide in 0.8 N ethanolic solution. After removal of the solvent by evaporation, the residue is recrystallised twice from a mixture of ethanol/ethylene glycol dimethyl ether. There is obtained in this manner a product of the stated composition, which gives in aqueous solution a buffer zone having a pH value of 6.1. From the limiting points of inflection of the buffer zone is found an equivalent weight of 331 (calculated 316).

EXAMPLE 13

38.6 g (0.10 mol) of 1,2,2,6,6-pentamethyl-4-(3,5-di-tert.-butyl-4-hydroxybenzylidene)-aminopiperidine are dissolved in 250 ml of ethanol, and 13.8 g (0.10 mol) of diethyl phosphite are added. The mixture is refluxed for 8 hours; the solvent is then evaporated off and the residue is recrystallised from acetonitrile. There is obtained in this manner diethyl-1-[(1,2,2,6,6-pentamethyl-4-piperidyl)-amino]-1-(3,5-di-tert.-butyl-4-hydroxyphenyl)-methylphosphonate in the form of a slightly yellow crystalline mass, which melts at 172°–174°.

Analysis: calculated: C 66.38%, H 10.18%, N 5.34%, P 5.90%; found: C 66.2%, H 10.3%, N 5.5%, P 6.0%.

The 1,2,2,6,6-pentamethyl-4-(3,5-di-tert.-butyl-4-hydroxybenzylidene)-aminopiperidine serving as starting product in this Example is obtained in the following manner: 17.0 g (0.10 mol) of 1,2,2,6,6-pentamethyl-4-aminopiperidine and 23.4 g (0.10 mol) of 3,5-di-tert.-butyl-4-hydroxybenzaldehyde are suspended in 230 ml of benzene and, with the addition of 10 g of p-toluenesulphonic acid, the suspension is dried for 5 hours in a water separator. The solvent is subsequently evaporated off, and the residue is recrystallised firstly from acetonitrile and then from cyclohexane to yield a yellow crystalline mass which melts at 141°–143°.

EXAMPLE 14

1,000 parts of polypropylene powder (melt index 1.5 g/10 minutes, 230°/2,160 g) and 1 part of pentaerythritoltetrakis-[ 3-(3', 5'-di-tert.-butyl-4-hydroxyphenyl)-propionate] and 5 parts of a stabiliser from Table I which follows are mixed in a drum mixer and the mixture is then granulated in an extruder at a temperature of 200°–220°.

The resulting granules are processed in the customary manner by means of an extruder with a sheet die to give a form and this is cut into small tapes, which are then stretched at elevated temperature to 6 times their length and wound up on a spool. The titer of the small tapes is 700–900 denier and their tear strength is 5.5–6.5 g/denier.

The small polypropylene tapes produced in this way are placed on sample carriers in a stress-free manner and exposed in a 1200 Xenotest apparatus. 5 test pieces, in each case, are taken out after various times and their tear strength is determined. The "protection factor", which is defined as follows:

"Protection factor" =

$$\frac{\text{Time of exposure of the light-stabilised sample up to a loss in tear strength of 50\%}}{\text{Time of exposure of the sample, which has not been light-stabilised, up to a loss in tear strength of 50\%}}$$

is taken as a measure of the protective action of the individual compounds.

The values obtained are given in Table I which follows:

Table I

| Stabiliser | Time (hours) of exposure up to a loss in tear strength of 50% | Protection factor |
|---|---|---|
| none | 140 | 1.0 |
| compound accord. to Example 2 | 1350 | 9.9 |
| compound accord. to Example 3 | 2730 | 20.0 |
| compound accord. to Example 4 | 1710 | 12.2 |

Table I-continued

| Stabiliser | Time (hours) of exposure up to a loss in tear strength of 50% | Protection factor |
|---|---|---|
| compound accord. to Example 5 | 1790 | 12.8 |
| compound accord. to Example 6 | 1440 | 10.3 |
| compound accord. to Example 7 | 2080 | 13.9 |

EXAMPLE 15

100 parts of polypropylene powder (Moplen, fibre grade, from Messrs. Montedison) are homogenised with 0.2 parts of octadecyl-$\beta$-(3,5-di-tert.-butyl-4-hydroxyphenyl)-propionate and 0.25 part of one of the stabilisers in Table II which follows for 10 minutes at 200° C. in a Brabender plastograph. The composition thus obtained is removed from the kneader as rapidly as possible and pressed in a toggle press to give a 2-3 mm thick sheet. Part of the resulting pressed blank is cut out and pressed between two high-gloss hard aluminium foils for 6 minutes at 260° and under a pressure of 12 tonnes, using a manual hydraulic laboratory press, to give a 0.5 mm thick film, which is immediately plunged into cold water. The 0.1 mm test film is produced from this 0.5 mm film under precisely the same conditions. 60 × 44 mm sections are now punched from this test film and exposed in a Xenotest 150. These test pieces are removed from the exposure apparatus at regular intervals and their carbonyl content is tested in an IR spectrophotometer. The increse in the carbonyl extinction on exposure is a measure of the photooxidative degradation of the polymer (see L. Blaban et al., J. Polymer Sci. Part C, 22, 1,059-1,071 (1969); J. F. Heacock, J. Polymer Sci. Part A-1, 22, 2,921-34 (1969) and D. J. Carlsson and D. M. Wiles, Macromolecules 2, 587-606 (1969)) and, according to experience, is associated with a deterioration in the mechanical properties of the polymer.

The time taken to reach a carbonyl extinction of about 0.300 is taken as a measure of the protective action.

The results are summarised in Table II.

Table II

| Stabiliser | Hours taken to reach a carbonyl extinction of 0.300 | Protection factor |
|---|---|---|
| None | 1,040 | 1.0 |
| Compound according to Example 1 | 4,810 | 4.6 |
| None | 1,210 | 1.0 |
| Compound according to Example 8 | 5,800 | 4.8 |

What is claimed is:

1. An amino-phosphate of the formula I

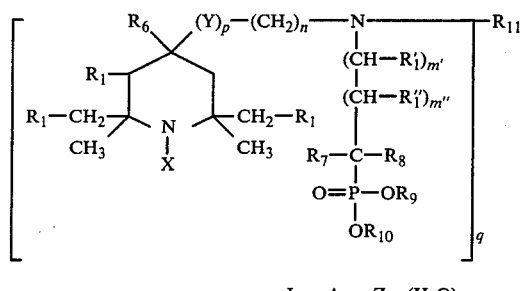

$$L_{r'} \cdot A_{r''} \cdot Z_t \cdot (H_2O)_s$$

in which $R_1$, $R'_1$ and $R''_1$ in each case independently of one anothe are hydrogen or $C_1$-$C_4$-alkyl, X denotes hydrogen, oxyl, $C_1$-$C_{12}$-alkyl, $C_3$-$C_6$-alkenyl, $C_3$-$C_4$-alkinyl, $C_2$-$C_{21}$-alkoxyalkyl, $C_7$-$C_8$-aralkyl, 2,3-epoxypropyl, an aliphatic acyl group with 1-4 C atoms or one of the groups —$CH_2COOR_2$, —$CH_2$—$CH(R_3)$—$OR_4$, —$COOR_5$ or —$CONHR_5$, in which $R_2$ is $C_1$-$C_8$-alkyl, $C_3$-$C_6$-alkenyl, phenyl, $C_7$-$C_8$-aralkyl or cyclohexyl and $R_3$ is hydrogen, methyl or phenyl and $R_4$ denotes hydrogen, an aliphatic or aromatic, araliphatic or alicyclic acyl group with 1-18 C atoms, in which the aromatic part can optionally be substituted by chlorine, $C_1$-$C_4$-alkyl or $C_1$-$C_8$-alkoxy and/or by hydroxyl, and $R_5$ denotes $C_1$-$C_{12}$-alkyl, cyclohexyl, phenyl or benzyl, $R_6$ is hydrogen, hydroxyl, $C_1$-$C_{12}$-alkylamino, cyano or $C_2$-$C_{13}$-alkoxycarbonyl, Y is —O— or

P is 0 or 1, if P is 1 n is 2,3 or 4 and, if P is 0, n is 0, 1 or 2, m' and m" in each case independently of one another are 0 or 1, $R_7$ is hydrogen, $C_1$-$C_{12}$-alkyl, $C_2$-$C_7$-alkenyl, cyclohexyl, cyclohexenyl, phenyl, phenyl which is substituted by $C_{1-C8}$-alkyl, $C_1$-$C_8$-alkoxy and/or hydroxyl, or $C_7$-$C_{13}$-aralkyl, 2-furyl or 2-pyridyl, $R'_1$ and $R_7$ conjointly form branched or unbranched $C_2$-$C_5$-alkylene, $R_8$ is hydrogen or methyl, $R_9$ is hydrogen, $C_1$-$C_{18}$-alkyl or $(M^{+w})w'$, in which M is a cation with a valency of w and in which w' is an integer which is equal to or smaller than w, $R_{10}$ is $C_1$-$c_{18}$-alkyl, q is 1 or 2 and, when q is 1, $R_{11}$ is hydrogen, $C_1$-$C_{18}$-alkyl, $C_2$-$C_4$-alkenyl, $C_3$-$C_{14}$-alkoxyalkyl, cyclohexyl, phenyl, phenyl which is substituted by $C_1$-$C_8$-alkyl or $C_1$-$C_8$-alkoxy, or $C_7$-$C_{13}$-aralkyl or $C_2$-$C_{18}$-acyl and, when q is 2, $R_{11}$ is $C_2$-$C_6$-alkylene or the bisacyl radical of a $C_2$-$C_{10}$-dicarboxylic acid, r' and r" independently of one another have an integral value or are the quotient of two integers between 0 and w, w denoting the valency of the cation mentioned under $R_9$, with the proviso that w/w'+r" equals q + r' when $R_9$ is $(M^{+w})/w'$ and that r' and r" are always 0 when $R_9$ is hydrogen or alkyl, L is a monovalent anion of a carboxylic acid with 1-24 C atoms or is a hydroxyl ion, A is an alkali metal cation and s has a value of 0 to 2, z denotes an amine of the general formula $R_{12}N(R_{13})R_{14}$, in which $R_{12}$ is $C_4$-$C_{12}$-alkyl, $C_3$-$C_{15}$-alkoxyalkyl, $C_7$-$C_8$-aralkyl, $C_5$-$C_8$-cycloalkyl or $C_2$-$C_3$-2-hydroxyalkyl and $R_{13}$ and $R_{14}$ independently of one another denote hydrogen, $C_1$-$C_4$-alkyl or $C_2$-$C_3$-2-hydroxyalkyl, or $R_{12}$ and $R_{13}$, together with N atom which links them, form a pyrrolidino, morpholino or piperidino radical which is optionally monosubstituted or polysubstituted by methyl, the said piperidino radical optionally carrying amino or $C_1$-$C_{12}$-alkylamino in the 4-position, and t is 0, 1 or 2, with the proviso that t is always 0 when $R_9$ is hydrogen or alkyl.

2. A compound according to claim 1, in which $R_1$, $R'_1$ and $R''_1$ are hydrogen or methyl, X is hydrogen, oxyl, $C_1$-$C_8$-alkyl, $C_3$-$C_4$-alkenyl or —alkinyl, $C_2$-$C_6$-alkoxyalkyl, $C_7$-$C_8$-aralkyl, acetyl, acryloyl or crotonoyl, or denotes one of the groups —$CH_2$—$COOR_2$, —$CH_2$—$CH(R_3)$—$OR_4$ or —$CONHR_5$, in which $R_2$ is $C_1$-$C_4$-alkyl, $C_3$-$C_4$-alkenyl, phenyl, $C_7$-$C_8$-aralkyl or cyclohexyl and $R_3$ is hydrogen, methyl or phenyl and $R_4$ denotes hydrogen or an aliphatic, aromatic, alicyclic or araliphatic acyl group with 1-18 C atoms, in which the aromatic part can optionally be substituted by chlorine, $C_1$-$C_4$-alkyl, $C_1$-$C_8$-alkoxy and/or hydroxyl, and $R_5$ is $C_1$-$C_{12}$-alkyl, $R_6$ is hydrogen, hydroxyl or $C_1$-$C_{12}$-alkylamino, Y is —O— or —NH—, p is 0 or 1 and, when p is zero n is 0, 1 or 2 and, when p is one n is 2 or 3, m' and m" independently of one another are 0 or 1, $R_7$ is hydrogen, $C_1$-$C_{11}$-alkyl, $C_2$-$C_4$-alkenyl, cyclohexyl, cyclohexenyl, phenyl or phenyl which is substituted by $C_1$-$C_4$-alkyl, $C_1$-$C_4$-alkoxy and/or hydroxyl or is $C_7$-$C_8$-aralkyl, $R'_1$ and $R_7$ conjointly form n-propylene or 2,2-dimethylpropylene, $R_8$ is hydrogen, $R_9$ is hydrogen, $C_1$-$C_8$-alkyl or $Mg^{+2}/w'$, $Ca^{+2}/w'$, $Sr^{+2}/w'$, $Ba^{+2}/w'$, $Zn^{+2}/w'$, $Cd^{+2}/w'$, $Al^{+3}/w'$, $Sn^{+2}/w'$, $VO^{+2}/w'$, $Cr^{+3}/w'$, $Co^{+2}/w'$, $Ni^{+2}/w'$, $(n-C_4H_9)_2Sn^{+2}/w'$ or $MoO_2^{+2}/w'$, in which w' is an integer which is identical to or smaller than the charge on these cations, $R_{10}$ is $C_1$-$C_8$-alkyl, q is 1, $R_{11}$ is hydrogen or $C_1$-$C_8$-alkyl, r' and r" independently of one another have an integral value or are the quotient of two integers between 0 and w, w denoting the valency of the cation indicated under $R_9$, with the proviso that $w/w' + r''$ equals $q + r'$ when $R_9$ is $(M^{+w})/w'$ and that r' and r" are always 0 when $R_9$ is hydrogen or alkyl, L is a monovalent anion of an aliphatic carboxylic acid with 2-18 C atoms or of an aromatic carboxylic acid with 7-18 C atoms or is a hydroxyl ion, A is a sodium cation or potassium cation and s has a value of 0 to 2, Z denotes an amine of the general formula $R_{12}N(R_{13})R_{14}$, in which $R_{12}$ is $C_4$-$C_8$-alkyl or $C_2$-$C_3$-2-hydroxyalkyl and $R_{13}$ and $R_{14}$ independently of one another are hydrogen, $C_4$-$C_8$-alkyl or $C_2$-$C_3$-2-hydroxylalkyl, or $R_{12}$ and $R_{13}$, together with the N atom which links them, form a piperidine radical which is monosubstituted or polysubstituted by methyl and optionally substituted in the 4-position by amino or $C_1$-$C_{18}$-n-alkylamino, and t is 0, 1 or 2, with the proviso that t is always 0 when $R_9$ is hydrogen or alkyl.

3. A compound according to claim 1, in which $R_1$, $R'_1$ and $R''_1$ are hydrogen or methyl, X is hydrogen, $C_1$-$C_4$-alkyl, allyl, benzyl, $C_2$-$C_6$-alkoxyalkyl, acetyl, acryloyl or crotonyl or is one of the groups —CH$_2$—COOR$_2$, —CH$_2$—CH(R$_3$)—OR$_4$ or —CONHR$_5$, in which $R_2$ is $C_1$-$C_4$-alkyl, $R_3$ is hydrogen or methyl, $R_4$ denotes hydrogen and $R_5$ is $C_1$-$C_4$-alkyl, $R_6$ is hydrogen or hydroxyl, Y is —O— or —NH—, is p is 0 or 1, and, when p is zero, n is 0, 1 or 2 and, when p is one, n is 2 or 3, m' and m" independently of one another are 0 or 1, $R_7$ is hydrogen, $C_1$-$C_7$-alkyl, phenyl or $C_7$-$C_8$-aralkyl, $R'_1$ and $R_7$ conjointly form n-propylene or 2,2-dimethylpropylene, $R_8$ is hydrogen, $R_9$ is hydrogen, $C_1$-$C_4$-alkyl or $Zn^{+2}/w'$, $Mg^{+2}/w'$, $Ca^{+2}/w'$, $Al^{+3}/w'$, $Co^{+2}/w'$ or $Ni^{+2}/w'$, w' being an integer which is identical to or smaller than the charge on the cations, $R_{10}$ is $C_1$-$C_6$-alkyl, q is 1, $R_{11}$ is hydrogen or $C_1$-$C_4$-alkyl, r' and r" independently of one another have an integral value or are the quotient of two integers between 0 and w, w denoting the valency of the cation indicated under $R_9$, with the proviso that $w/w' + r''$ equals $q + r'$ when $R_9$ is $(M^{+w})/w'$ and that r' and r" are always 0 when R is hydrogen or alkyl, L is a monovalent anion of an aliphatic carboxylic acid with 2-18 C atoms or is a hydroxyl ion, A is a sodium cation or potassium cation, s has a value of 0 to 2 and Z denotes an amine of the general formula $R_{12}N(R_{13})R_{14}$, in which $R_{12}$ is $C_4$-$C_8$-alkyl or 2-hydroxyethyl and $R_{13}$ and $R_{14}$ independently of one another are hydrogen, $C_4$-$C_8$-alkyl or 2-hydroxyethyl, or $R_{12}$ and $R_{14}$, together with the N atom which links them, form 4-n-octylamino-2,2,6,6,-tetramethylpiperidine, and t is 0, 1 or 2, with the proviso $R'_1 R''_1 9$ is hydrogen or alkyl. $R'_1$ 4. A compound according to claim 1 in which $R_1$ is hydrogen, $R_1'$ and $R_1''$ are hydrogen or methyl, X is hydrogen, methyl, allyl, benzyl or acetyl, $R_6$ is hydrogen or hydroxyl, p is 0 or 1 and, when p is zero n is 0, 1 or 2 and, when p is one, n is 3, m' and m" independently of one another are 0 or 1, $R_7$ is hydrogen, $C_1$-$C_6$-alkyl or phenyl, $R_1'$ and $R_7$ conjointly form n-propylene or 2,2-dimethylpropylene, $R_8$ is hydrogen, $R_9$ is hydrogen, methyl, ethyl or $Zn^{+2}/w'$, $Mg^{+2}/w'$, $Al^{+3}/w'$, $Co^{+2}/w'$, or $Ni^{+2}/w'$, w' being an integer which is identical to or smaller than the charge on the cations, $R_{10}$ is $C_1$-$C_4$-alkyl, q is 1, $R_{11}$ is hydrogen, r' and r" independently of one another have an integral value or are the quotient of two integers between 0 and w, w denoting the valency of the cation indicated under $R_9$, with the proviso that $w/w' + r''$ equal $g + r'$ when $R_9$ is $(M^{+w})/w'$ and that r' and r" are always 0 when $R_9$ is hydrogen or alkyl, L is a monovalent anion of an alkanecarboxylic acid with 2-12 C atoms or is a hydroxyl ion, A is a sodium cation, s has a value of 0 to 2 and Z denotes an amine of the general formula $R_{12}N(R_{13})R_{14}$, in which $R_{12}$ is $C_4$-$C_8$-alkyl, $R_{13}$ is n-butyl and $R_{14}$ is hydrogen, and t is 0 or 1 or 2, with the proviso that t is always 0 when $R_9$ is hydrogen or alkyl.

5. A compound according to claim 1, namely Ni-di-{ethyl-1-[(1,2,2,6,6-pentamethyl-4-piperidyl)-amino]-n-heptyl-phosphonate}-monohydrate having the formula

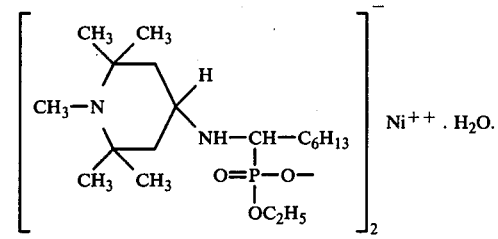

6. A compound according to claim 1, namely Co-di-{ethyl-1-[(1,2,2,6,6-pentamethyl-4-piperidyl)-amino]-n-heptyl-phosphonate}-monohydrate having the formula

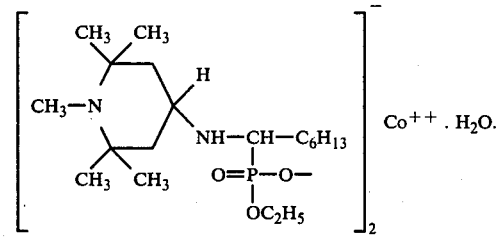

7. A compound according to claim 1, namely Zn-di-{ethyl-1-[(1,2,2,6,6-pentamethyl-4-piperidyl)-amino]-n-heptyl-phosphonate}-sodium acetate having the following formula 8. A compound according to claim 1, namely Al-tri-{ethyl-1-[(1,2,2,6,6-pentamethyl-4-piperidyl)-amino]-n-heptyl-phosphonate} having the following formula

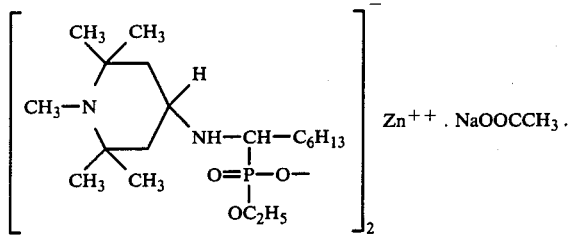

9. A compound according to claim 1, namely diethyl-3-[(2,2,6,6-tetramethyl-4-piperidyl)-amino]-n-propyl-phosphonate having the following formula

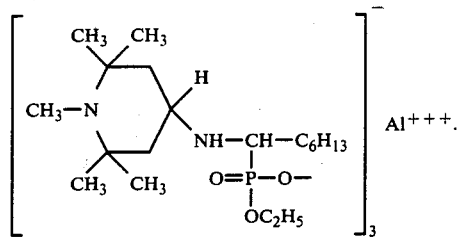

10. Composition of matter consisting of a polymer and at least one compound of the formula I of claim 1.

11. Composition of matter according to claim 10 wherein the polymer is a polyolefine, a styrene polymer, a polyamide or a polyurethane.

12. Process for stabilizing polymers, wherein at least one compound of the formula I of claim 1 is added to the polymer.

* * * * *